(12) United States Patent
Okamoto

(10) Patent No.: US 7,841,054 B2
(45) Date of Patent: Nov. 30, 2010

(54) BODY CAVITY SEALING MEMBER, METHOD FOR MANUFACTURING THE SAME, AND CORPSE TREATMENT DEVICE

(75) Inventor: Toshiki Okamoto, Hiroshima (JP)

(73) Assignee: Risa Nishihara (JP)

( * ) Notice: Subject to any disclaimer, the term of this patent is extended or adjusted under 35 U.S.C. 154(b) by 306 days.

(21) Appl. No.: 11/663,778

(22) PCT Filed: Oct. 18, 2004

(86) PCT No.: PCT/JP2004/015374
§ 371 (c)(1),
(2), (4) Date: Mar. 26, 2007

(87) PCT Pub. No.: WO2006/043306
PCT Pub. Date: Apr. 27, 2006

(65) Prior Publication Data
US 2007/0214618 A1    Sep. 20, 2007

(51) Int. Cl.
*A01N 1/00* (2006.01)
(52) U.S. Cl. .......................... 27/21.1; 27/24.1; 27/24.2; 604/365; 604/381; 604/378; 604/366; 604/386
(58) Field of Classification Search ............... 27/21.1, 27/24.1, 24.2
See application file for complete search history.

(56) References Cited

U.S. PATENT DOCUMENTS 3,527,203 A * 9/1970 Gravlee ...................... 600/563
3,815,601 A * 6/1974 Schaefer ....................... 604/15
4,241,735 A * 12/1980 Chernov ...................... 606/192
4,265,244 A * 5/1981 Hill .............................. 604/175

(Continued)

FOREIGN PATENT DOCUMENTS

EP    0159671 A2    10/1985

(Continued)

OTHER PUBLICATIONS

T.Mausser; European Search Report; Nov. 18, 2008; EP 04792543.

(Continued)

*Primary Examiner*—Tatyana Zalukaeva
*Assistant Examiner*—Ilya Y Treyger
(74) *Attorney, Agent, or Firm*—Studebaker & Brackett PC; Donald R. Studebaker

(57) ABSTRACT

This invention aims at developing a sanitary body cavity sealing device which prevents leakage of substances in the rectum of a corpse due to anal muscle relax after die, simplifies the postmortem treatment work for persons working on it or nurses and prevents infection to the persons, nurses or those around due to leakage of body internal substances. The body cavity sealing member (10) is made of porous fiber elements that absorb water on contact with body fluids in a body cavity to expand up to approximately 2.5 or more times its diameter, its end part (15) is cut into a tapered shape and the cut surface (15) is processed, for example, by heat treatment, to form a smooth surface. By inserting the body cavity sealing member (10) with the end part first into the anus, it can be inserted into the rectum without being interfered with by the inner walls of the anus and rectum.

5 Claims, 11 Drawing Sheets

U.S. PATENT DOCUMENTS 5,873,971 A * 2/1999 Balzar ............... 156/217

FOREIGN PATENT DOCUMENTS

| EP | 0 763 365 | A1 |   | 3/1997 |
|----|-----------|----|---|--------|
| JP | 06-304202 | A  |   | 11/1994 |
| JP | 09-103480 | A  |   | 4/1997 |
| JP | 11-200209 | A  |   | 7/1999 |
| JP | 2001-161733 |  | * | 6/2001 |
| JP | 2002-087901 | A |  | 3/2002 |
| JP | 2002085493 | A |  | 3/2002 |
| JP | 2002-200126 | A |  | 7/2002 |
| JP | 2002-275001 |  |  | 9/2002 |
| JP | 2002248140 | A |  | 9/2002 |
| JP | 2003-111830 |  | * | 4/2003 |
| JP | 2003-111830 | A |  | 4/2003 |

OTHER PUBLICATIONS

International Search Report for PCT/JP2004/015374 Dated Nov. 22, 2004.

Japanese Office Action "Notice of Reasons for Rejection" dated Jun. 29, 2010; Japanese Patent Application No. 2006-542125; with translation.

* cited by examiner (×30)

(×60)

(×30)

(×60)

US 7,841,054 B2

BODY CAVITY SEALING MEMBER, METHOD FOR MANUFACTURING THE SAME, AND CORPSE TREATMENT DEVICE

TECHNICAL FIELD

This invention relates to corpse's body cavity sealing members for preventing leakage of internal substances from body cavities of a corpse and its attendant contamination to the surroundings and infection to those around, methods for manufacturing the same and corpse treatment devices using the body cavity sealing members, and particularly relates to a corpse's body cavity sealing member for preventing leakage of internal substances from cavities of a lower body, such as the anus or vagina, and its attendant contamination to the surroundings and infection to those around, a method for manufacturing the same and a corpse treatment device using the body cavity sealing member.

BACKGROUND ART

Usually, after humans die, muscles of their body cavities become flaccid so that waste materials in the body cavities often leak out. Further, because of intravenous drip during medical treatment in life, the bodies after death often contain a large amount of body fluids. In particular, as for a body cavity in their low bodies, i.e., the anus, the anal muscle is relaxed to open the anus, resulting in leakage of internal waste materials. Furthermore, if they are female, the vaginal cavities often leak out a large amount of body fluids. To prevent these leakages, the anus and vaginal cavity is filled with a huge amount of absorbent cotton before the occurrence of postmortem rigidity.

Such work is often carried out by a nurse. Not only the work is troublesome and unsanitary but also the worker at work may be infected with germs or viruses from the leaked substances. Therefore, there is a strong need to surely prevent such infection. Traditional countermeasures to the infection, however, are not good in terms of feasibility.

For example, a diaper is used in many cases in order to prevent leakage of internal waste materials in cavities of parts of a corpse, particularly, in cavities of the lower body such as the anus or vaginal cavity. In these cases, the diaper cannot fully prevent the leakage of waste materials, leading to contamination due to leakage. In addition, the nurse inevitably contacts the waste materials during diaper cleaning for replacement. For these reasons, if the body is a germ carrier, those around may be infected.

Techniques are known which eliminate the above problems and prevent leakage of internal substances in corpse lower body cavities, such as the anus or vaginal cavity, and in which body cavity sealing members are directly inserted into lower body cavities, such as the rectum or vaginal cavity. (See, for example, Japanese Unexamined Patent Publication Nos. 2001-161733 and 2003-111830)

As shown in FIG. 20, the body cavity sealing member in Japanese Unexamined Patent Publication No. 2001-161733 is designed so that a plug part (101) is inserted into the anus, a gas injector (Y) is then inserted into an opening (108) located at a joint (A) between the plug part (101) and an anus abutment member (102) and the plug part (101) is charged with gas. The gas flows from the inside of the plug part (101) through a gas guide hole (106) to open a non-return valve (107), is fed to an control chamber (105) and expands the control chamber (105). Thus, a flexible member (104) comes into tight contact with the inner wall of the anus to seal the anus. Reference numeral 112 denotes a lubricant layer.

As shown in FIGS. 21 and 22, the body cavity sealing member 200 in Japanese Unexamined Patent Publication No. 2003-111830 is composed of a columnar superabsorbent fiber molded object 201, a water-soluble sheet 202 sheathing the molded object 201, and a lubricant 203 covering the sheet 202. The body cavity sealing member 200 has one end tapered to facilitate its insertion. The superabsorbent fiber molded object 201 disclosed in the publication is made of water-swellable fibers (trade name: LANSEAL®F manufactured by Toyobo Co., Ltd.) of double-layer structure that has an inner layer made of an acrylic fiber serving as a core and a superabsorbent outer layer placed to surround the inner layer and processed to swell after absorbing water. The surface of the superabsorbent fiber molded object 201 is wrapped in a thin water-soluble sheet. The body cavity sealing member 200 is enveloped in a bag 204 made of a protective covering material.

Problems to be Solved

As for the body cavity sealing member 100 in Japanese Unexamined Patent Publication No. 2001-161733, the plug part (101) is inserted in the anus and part of the anus then fills in between the expanded control chamber (105) and the anus abutment member (102). This prevents the plug part (101) from entering deep in the anus or getting out of the anus.

Since, however, the anus abutment member (102) protrudes from the anus and is exposed to the outside, the body does not have a natural appearance and shows up that it has undergone some kind of treatment. Therefore, the use of this member is often rejected by bereaved families or nurses who treat bodies.

Further, the above member involves the use of a tool Y for expanding it with gas and also needs to be sealed against leakage of the gas. Therefore, the member is relatively hard to handle as a body cavity sealing member and cannot be said to have a sufficient anti-leakage function. In particular, since the member is not of a type that expands by absorbing body fluids, it may leak out body fluids if even a slight clearance exists therein, which does not provide a sufficient function as a body cavity sealing member. In addition, the control of gas pressure is difficult.

In using the body cavity sealing member 200 in Japanese Unexamined Patent Publication No. 2003-111830, the bag 204 is first opened to take out the body cavity sealing device 200. Then, the tapered side of the sealing member 200 is oriented to the anus of a body and, in this position, the sealing member 200 is pushed through the anus into the rectum. Since the body cavity sealing member 200 is pushed through the anus in the rectum, it cannot be seen from the outside of the body. Therefore, the use of this member will not be rejected by bereaved families or others concerned on the ground of its appearance. Further, the body cavity sealing member 200 is formed so that a superabsorbent fiber molded object 201 is wrapped in a water-soluble sheet 202 and a lubricant 203 such as glycerin is further applied to the outer surface of the sheet 202. In this manner, this member is contrived to easily slide in the anus when forcedly inserted through the anus.

This member, however, may not enter through the anus into the rectum well depending upon individual skill levels of nurses or others handling it. The reason is believed to be as follows: Even if the fiber molded object 201 is wrapped in the water-soluble sheet 202 and the lubricant 203 is applied to the sheet 202, both the layers of the water-soluble sheet 202 and the lubricant 203 are thin and soft. Therefore, on contact with muscles of the anus inner wall, such a thin and soft surface cannot slide on the muscles well to enter the rectum. Further, the sheet 202 wrapped around the fiber molded object 201 is twisted and overlapped itself at the tapered end of the fiber molded object 201. This also provides an inconvenient configuration for insertion work.

Particularly, the work for wrapping the fiber molded object 201 in the water-soluble sheet 202 is carried out by covering all sides of the fiber molded object 201 with a rectangular water-soluble sheet 202 and fitting the water-soluble sheet 202 to the fiber molded object 201 in the following manner: part of the water-soluble sheet 202 at the tapered end of the fiber molded object 201 is pinched and twisted while being wrung to the tapered shape of the fiber molded object 201, and part of the water-soluble sheet 202 at the other end of the fiber molded object 201 is also pinched and twisted to overlap itself.

Because of the above manner, the work for fitting the water-soluble sheet 202 to all sides of the fiber molded object 201 is manual, less likely to be automated and not suitable for mass production methods. Further, if the worker strongly twists the water-soluble sheet 202 wrapped around the fiber molded object 201, it may break. On the contrary, if the worker weakly twists the water-soluble sheet 202, it may peel off from the fiber molded object 201. Therefore, the fitting work lacks stability. The fitting work also leads to increased manufacturing cost.

The present invention has been made in view of the foregoing points and, therefore, its object is to provide a sanitary body cavity sealing member and a manufacturing method for the same which prevent leakage of substances in cavities of the lower part of a corpse, such as the rectum and vaginal cavity, simplify the body treatment work for persons working on it and nurses and prevent infection to the persons, nurses or those around due to leakage of body internal substances. Further, another object of the present invention is to provide a manufacturing method which is excellent in productivity of body cavity sealing members and can provide stable body cavity sealing members. A still another object of the present invention is to provide a corpse treatment device in the form of a kit including not only a body cavity sealing member for sealing a cavity in the lower part of a corpse but also anti-leakage members for other body cavities, in particular, anti-leakage members for preventing leakage of body fluids from the throat and mouth.

DISCLOSURE OF THE INVENTION

The body cavity sealing member of the present invention is a body cavity sealing member that, when inserted into a body cavity of a corpse, absorbs body fluids to expand, resides on the spot and seals the passage of the body cavity to prevent leakage of the body fluids, wherein the body cavity sealing member is formed of a molded object molded into a substantially columnar shape by bundling a plurality of fiber elements of double-layer structure and formed so that at least one end part of the molded object is tapered toward the end thereof, the surface of the tapered end part is formed of distal ends of the fiber elements, the distal ends being processed to fuse one fiber element to another, and each of the fiber elements includes an inner layer which is a core made of an acrylic fiber and an outer layer which is formed to surround the inner layer and has a higher water-absorbability and higher swellability than the inner layer, and has the property of absorbing body fluids in the body cavity to expand up to approximately 2.5 or more times the diameter thereof.

The surface of the tapered end part preferably has a smaller coefficient of friction after being processed than before.

The fiber elements exposed at the surface of the tapered end part are preferably formed by heat treatment.

The heat treatment is preferably implemented by melting the fiber elements exposed at the surface of the tapered end part to fuse one fiber element to another.

The surface of the tapered end part preferably has a higher hardness than the surface of the remaining columnar part.

Preferably, the outer layer is made of hydrophilic crosslinked polymer obtained by hydrophilically crosslinking an acrylic fiber and each fiber element has the property of absorbing body fluids to expand up to five or more times the diameter thereof and has a degree of water swelling of 5 to 200 cc/g.

The corpse treatment device of the present invention comprises: the above body cavity sealing member; a syringe filled with a jelly substance which contains superabsorbent resin and is to be infused into the throat of a corpse; an insertion tube connectable to an infusion head of the syringe; a cover member for covering the insertion tube; a cotton piece for a mouth to which a jelly substance containing superabsorbent resin is adhered; and a bag for containing the body cavity sealing device, the syringe, the insertion tube, the cover member and the cotton piece, wherein the insertion tube comprises: a tube body which is made of flexible synthetic resin and configured to be inserted through a nostril into a throat; and a connecting part provided at the rear end of the tube body and connectable to the syringe, and has a tube opening formed at the front end of the tube body.

Gloves for handling components of the corpse treatment device are preferably further contained in the bag.

A paper sheet for wiping hands is preferably further contained in the bag.

Sealing members for an earplug and a nose plug are preferably further contained in the bag.

A vessel containing a lubricant is preferably further contained in the bag.

A container bag for containing the used components including the body cavity sealing device, the syringe, the insertion tube and the cover member is preferably further contained in the bag.

The method for manufacturing a body cavity sealing member of the present invention is a method for a body cavity sealing member that, when inserted into a body cavity of a corpse, absorbs body fluids to expand, resides on the spot and seals the passage of the body cavity to prevent leakage of the body fluids, and the method comprises: bundling a plurality of fiber elements of double-layer structure, each including an inner layer which is a core made of an acrylic fiber and a superabsorbent outer layer which is formed to surround the inner layer, to form a columnar molded object of the fiber elements which has the property of rapidly absorbing water on contact with body fluids in the body cavity to expand up to approximately 2.5 or more times the diameter thereof; cutting an end part of the columnar molded object to taper toward the end of the molded object; and subjecting the cut surface of the end part of the molded object to heat treatment.

The heat treatment is preferably carried out in a temperature range of 150 to 260° C. for 3 to 25 seconds. If the heating temperature is low, the surfaces of the fiber elements fall short of melting, resulting in unsmooth surfaces. On the contrary, if the heating temperature is high, the surfaces of the fiber elements are burned, resulting in an unserviceable product. Further, if the heating time is short, the surfaces of the fiber elements fall short of melting, resulting in unsmooth surfaces. On the contrary, if the heating time is long, the surfaces of the fiber elements are burned, resulting in an unserviceable product. Therefore, the above heating temperature range and the above heating time range are preferable. The heat treatment is more preferably carried out in a temperature range of 180 to 220° C. for 7 to 15 seconds.

The cutting preferably comprises forming an end part of the columnar molded object in a tapered shape with a cutting blade.

The heat treatment is preferably implemented by pressing the tapered end part of the body cavity sealing member against a die which has a recess for receiving the tapered end part of the body cavity sealing member and in which the surface of the recess is heated.

BEST MODE FOR CARRYING OUT THE INVENTION

Embodiments of the present invention will be described below in detail with reference to the drawings.

First Embodiment

Figure 1:
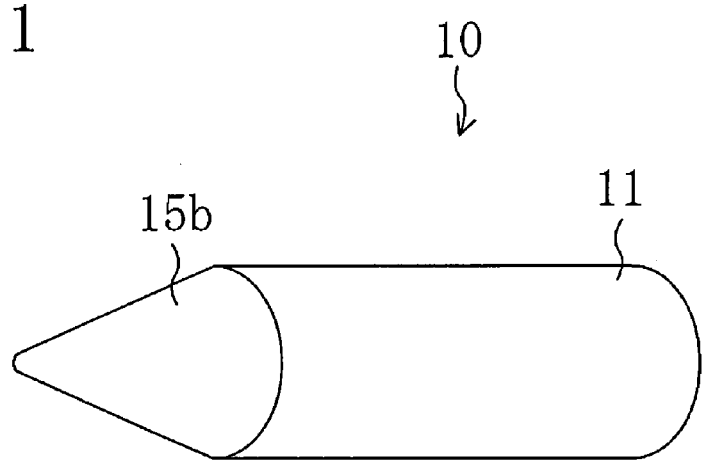
FIG. 1 shows a body cavity sealing member according to a first embodiment of the present invention.
Figure 2:
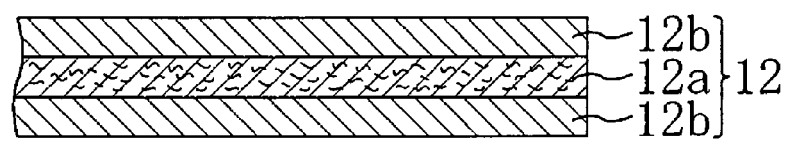
FIG. 2 shows a partly enlarged cross-sectional view of a porous fiber element in the body cavity sealing member.

As shown in FIG. 1, a body cavity sealing member 10 is formed of a columnar superabsorbent, porous fiber molded object 11 having one end part tapered toward its distal end. The fiber molded object 11 is a porous molded object obtained by bundling water-swellable fibers 12 of cross section shown in FIG. 2 into a columnar shape. The fiber molded object 11 employs as superabsorbent fibers 12 a superabsorbent, porous fiber molded object (trade name: LANSEAL®F manufactured by Toyobo Co., Ltd.) that expands up to 2.5 or more times its diameter by absorbing water. The water-swellable fiber 12 is a porous fiber of double-layer structure that has an inner layer 12a made of an acrylic fiber serving as a core and a superabsorbent outer layer 12b placed to surround the inner layer 12a and processed to swell after absorbing water. The prepared molded object 11 has a diameter of 22 mm and a length of 80 mm.

Figure 3:
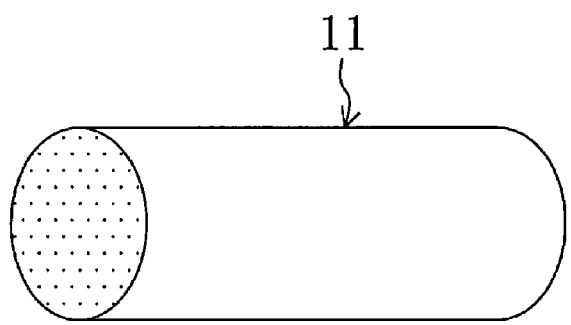
FIG. 3 shows a perspective view of the body cavity sealing member when still having a rod shape.
Figure 4:
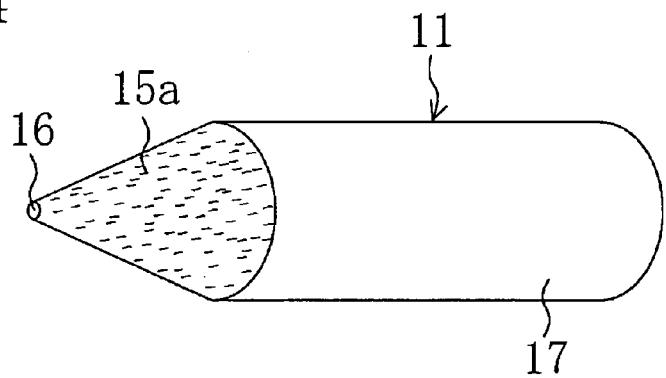
FIG. 4 shows a perspective view of the body cavity sealing member when its one end part is cut.
Figure 5:
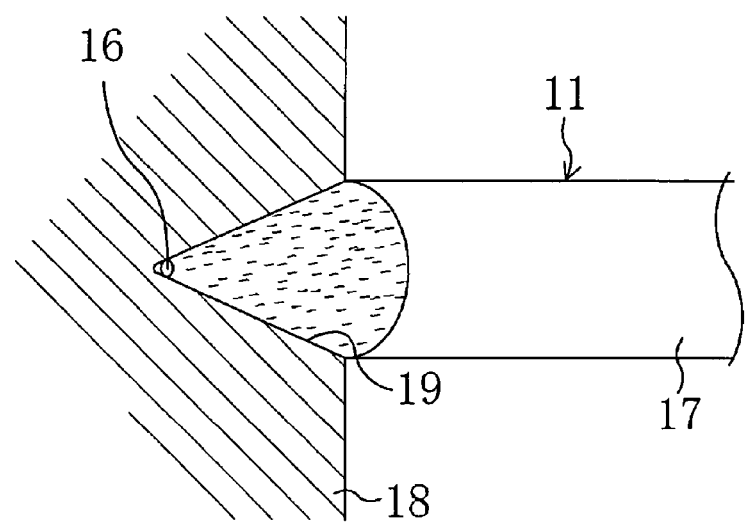
FIG. 5 shows a perspective view of the body cavity sealing member when its one end part undergoes heat treatment.

FIGS. 3 to 5 show process steps for forming one end part of the body cavity sealing member 10. As shown in FIG. 3, a columnar superabsorbent fiber molded object 11 of predetermined length is prepared. One end of the molded object 11 is cut by a cutting blade (not shown) to form a tapered (substantially conical) cut surface 15a as shown in FIG. 4. The part of the molded object 11 other than the substantially conical tapered part is a columnar part 17. Reference numeral 16 denotes an apex. Then, a die 20 for heating the cut surface 15a is prepared. The die 20 has a substantially conical recess 19 that can abut on the cut surface 15a. The recess 19 is heated to approximately 200° C. As shown in FIG. 5, the cut surface 15a of the body cavity sealing member 10 is brought to lightly bear on the recess 19 of the die 18 to melt its superficial layer by heat. In this embodiment, the heating temperature and heating time are set at 200° C. and 10 seconds, respectively. As a result, as shown in FIG. 1, a body cavity sealing member 10 can be obtained which has a smoothed cut surface 15b. The cut surface 15a as cut and the cut surface 15b after heat treatment will be described in detail later.

Figure 6:
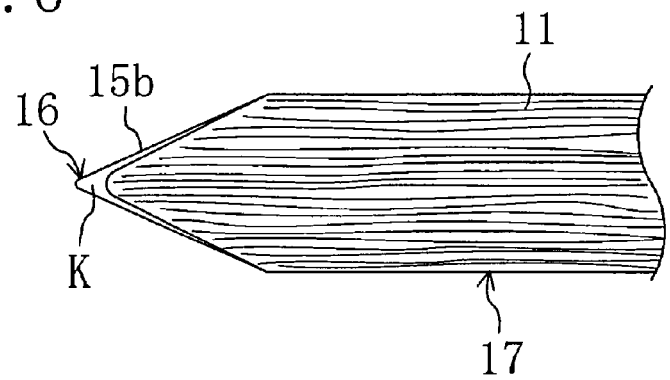
FIG. 6 shows a partly cross-sectional view of a cut surface of the body cavity sealing member shown in FIG. 5.

FIG. 6 shows a cross-sectional view of the cut surface 15b after heat treatment. The cut surface 15b is melted at its superficial layer to harden so that its hardness becomes higher than that of the columnar part 17. The hardened layer K of the cut surface 15b gradually becomes thicker toward the distal end (apex) 16 of the tapered part and gradually becomes thinner toward the rear end (columnar part). The reason why the above thickness differences occur in the hardened layer is believed to be that even if the temperature of the recess 19 of the die 18 is uniform, the cut surface 15a has a smaller amount of fiber elements at the apex 16 and a larger amount of fiber elements at a portion toward the rear end. Also in terms of the hardness of the most superficial layer of the cut surface 15b, the apex 16 is slightly greater than the portion toward the rear end.

Since the cut surface 15b is hardened to have a high hardness, the body cavity sealing member 10 has a merit that when it is inserted into a body cavity of a lower body, for example, through the anus into the rectum, it can be inserted deeply without deforming the cut surface 15b even if it contacts the inner wall of the anus or rectum. In particular, since the apex 16 has a higher hardness, this is advantageous in preventing its deformation.

While the recess 19 of the die 18 almost conforms to the shape of the cut surface 15a, the most distal end (apex) 16 of the cut surface 15a is formed so as not to contact the recess 21 of the die 20. If the apex 16 contacts the recess 21, the entire cut surface 15a will be heated to melt. In this case, if the entire cut surface 15a is heated until becoming smoothed, the apex 16 may be excessively heated to burn. Therefore, the apex 16 is intentionally formed to make no contact with the recess 19.

In this embodiment, since the control on the heating temperature and time is easy, the apex 16 is formed to make no contact with the recess 19 of the die 18. If, however, the heating temperature and time can be controlled with high precision, the entire cut surface 15b including the apex 16 may contact the recess 19.

In order to allow the entire cut surface 15b to form a smooth surface, the depth of the recess 19 of the die 18 is preferably the depth at which the entire cut surface 15b just fills in the recess 19 or larger than the depth of the cut surface 15b.

Next, a description will be made of the surface states of the cut surfaces 15a and 15b.

Figure 7:
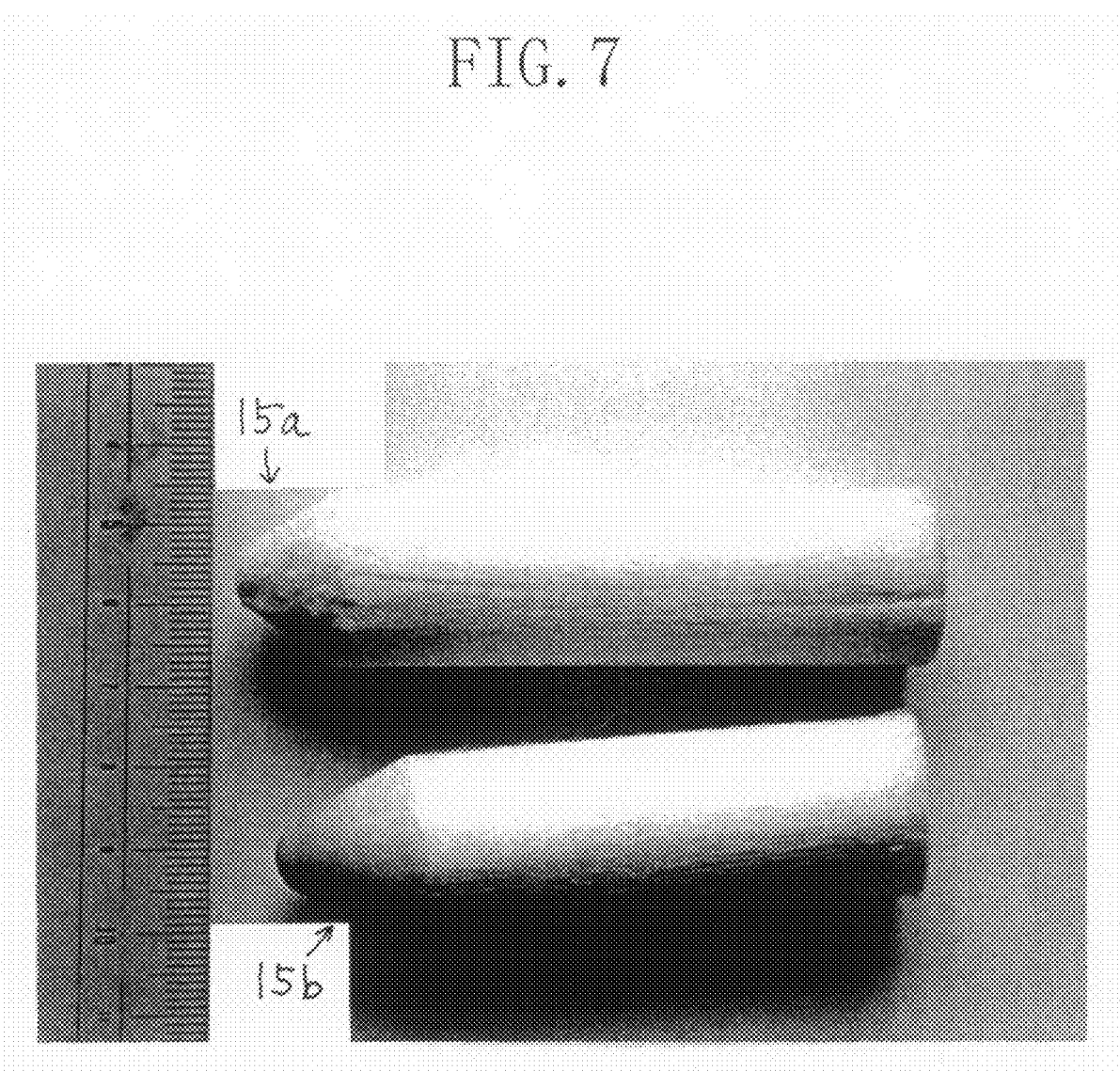
FIG. 7 shows a perspective view of the appearance of the body cavity sealing member, in which the upper part shows a state before heat treatment and the lower part shows a state after heat treatment.
Figure 8:
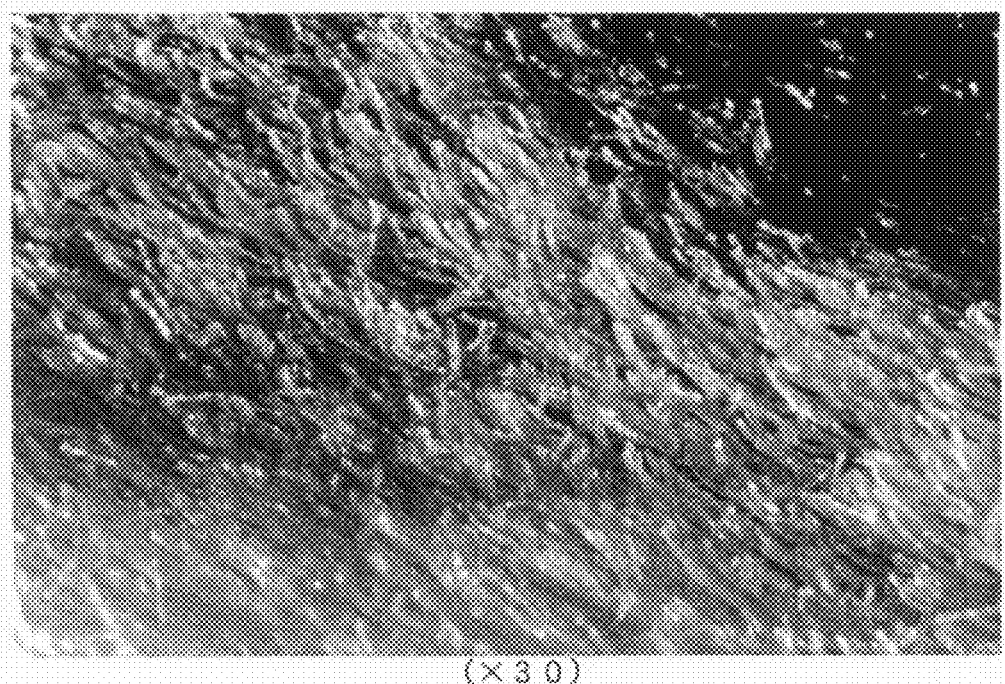
FIG. 8 shows a photograph in which the cut surface of the body cavity sealing member (before heat treatment) is magnified 30 times by a microscope.
Figure 9:
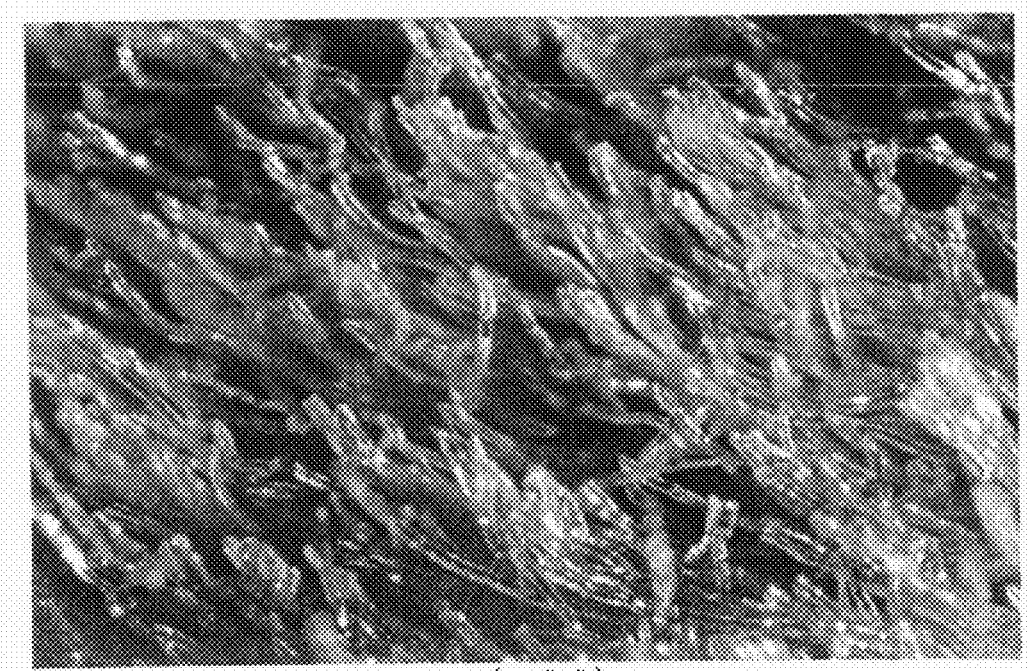
FIG. 9 shows a photograph in which the cut surface of the body cavity sealing member (before heat treatment) is magnified 60 times by a microscope.
Figure 10:
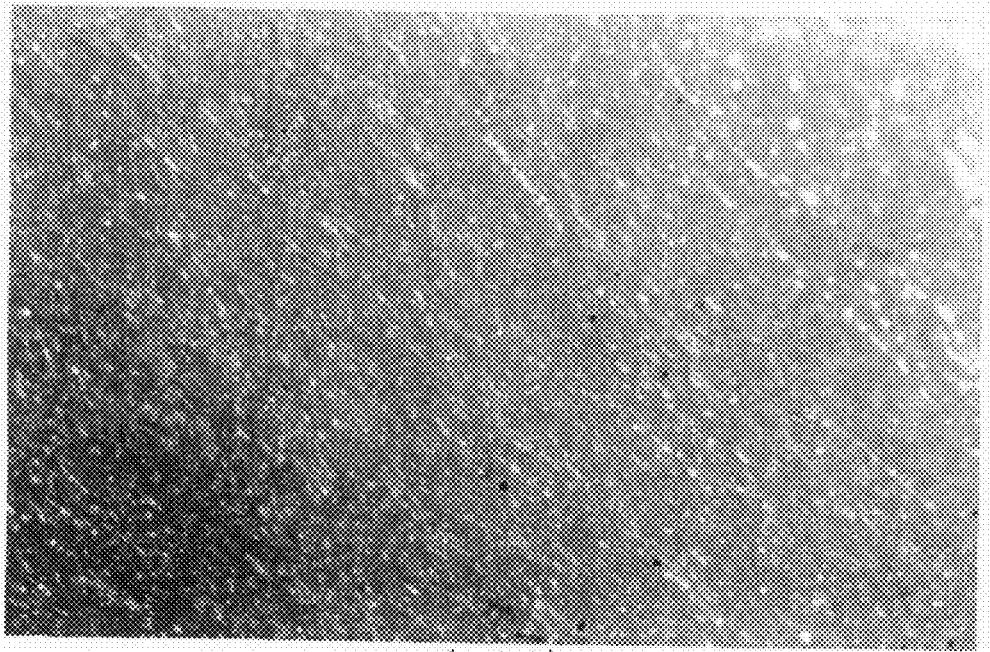
FIG. 10 shows a photograph in which the cut surface of the body cavity sealing member (after heat treatment) is magnified 30 times by a microscope.
Figure 11:
FIG. 11 shows a photograph in which the cut surface of the body cavity sealing member (after heat treatment) is magnified 60 times by a microscope.

The upper part of FIG. 7 shows the appearance of the fiber molded object 11 shown in FIG. 4, i.e., the fiber molded object 11 having a cut surface 15a obtained by cutting its one end part with a cutting blade or the like, and the lower part of FIG. 7 shows the appearance of the fiber molded object 11 shown in FIG. 4, i.e., the fiber molded object 11 having a cut surface 15b subjected to heat treatment. FIGS. 8 and 9 show photographs in which part of the cut surface 15a shown in the upper part of FIG. 7 is magnified 30 times and 60 times, respectively, by a microscope. FIGS. 10 and 11 show photographs in which part of the cut surface 15b shown in the lower part of FIG. 7 is magnified 30 times and 60 times, respectively, by a microscope.

As shown in FIGS. 8 and 9, the cut edges of the fibers 12 (the distal ends of the fiber elements) are exposed at random on the cut surface 15a. When the cut surface 15a is touched by hand from the apex 16 toward the columnar part 17, it feels rough and in some regions feels prickly. If, in this surface state, the fiber molded object 11 is inserted into a body cavity of a lower body, for example, through the anus into the rectum, the cut surface 15a sticks in the inner wall of the anus or rectum or provides a large frictional resistance, which hinders the fiber molded object 11 from entering inward.

On the other hand, as shown in FIGS. 10 and 11, the cut surface 15b of the fibers 12 in the first embodiment of the present invention has a smoothness due to melting of fiber elements by heat. In the cut surface 15b, the fiber elements are fused together to harden. The distal ends of the fiber elements on the cut surface 15a formed by cutting are hardly found to be exposed as they are. If the cut surface 15b is touched by hand from the apex 16 toward the columnar part 17, it does not feel rough and, particularly, never gives a prickly feel but feels smooth. The reason is that the distal ends of the fiber elements exposed at the cut surface 15a are fused to other fiber elements so that the heat-treated cut surface 15b has a smaller coefficient of friction than the cut surface 15a before heat treatment. The smoothness of the heat-treated cut surface 15b allows the fiber molded object 11 to be inserted deeply without resistance even if it contacts the inner wall of the anus or rectum.

The columnar part 17 of the fiber molded object 11 is given a certain degree of smoothness when a rod-shaped fiber molded object 11 is formed. Therefore, the columnar part 17 can be inserted into the anus simply by applying the lubricant to its surface, and there is no need for special measures to slide it in the anus except for the application of the lubricant.

Next, a description will be made of an example of how to use the body cavity sealing member 10 formed of a tapered fiber molded object 11.

Figure 12:
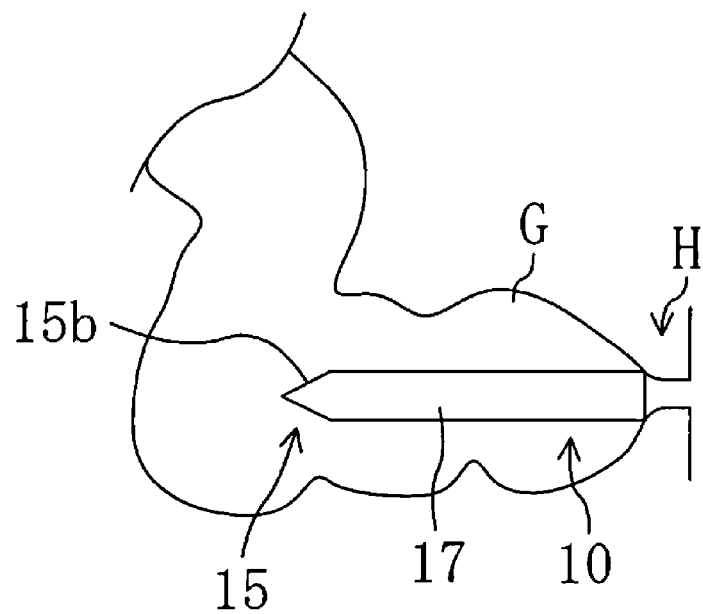
FIG. 12 is a view illustrating a condition of the body cavity sealing member when it is being inserted into the rectum.
Figure 13:
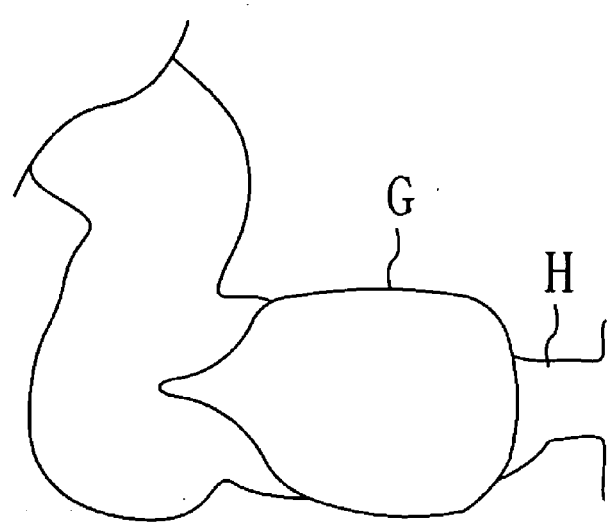
FIG. 13 is a view illustrating a condition of the body cavity sealing member after it is inserted in the rectum.

FIGS. 12 and 13 show an example of use of the body cavity sealing member 10 for sealing the rectum.

FIG. 12 is a view illustrating a condition of the body cavity sealing member 10 for a rectum when it is inserted through the anus H into the rectum G, and FIG. 13 is a view illustrating a condition of the body cavity sealing member 10 for a rectum when it expands. The lubricant 35 is applied to the cut surface 15 and the columnar part 17 of the body cavity sealing member 10, and the body cavity sealing member 10 is then inserted with the tapered cut surface 15b first into the anus H. Since the cut surface 15b is melted by heat, the lubricant 35 is hard to penetrate through the cut surface 15b into the fiber molded object 11 and likely to reside on the cut surface 15b when it is applied to the cut surface 15b. Therefore, even if the cut surface 15b comes into contact with the inner wall of the anus H, it slides on the inner wall and easily enters inward. Further, since the cut surface 15b is hardened, this effectively prevents the cut surface 15b from deforming on contact with the inner wall of the anus H or rectum G and facilitates the further insertion of the body cavity sealing member 10.

After the insertion, body fluids in the rectum G are absorbed in the fiber molded object 11. The superabsorbent outer layer 12b of each water-swellable fiber 12 in the fiber molded object 11 rapidly expands so that the outer surface of the fiber molded object 11 reaches the inner wall of the rectum G. As a result, the rectum G is sealed against leakage of body fluids. In particular, since the cut surface 15b is melted by heat, it is resistant to penetrating body fluids and resistant to expansion even when absorbing body fluids. Therefore, body fluids tend to be absorbed more rapidly into the columnar part 17 of the body cavity sealing member 10. As a result, the columnar part 17 of the body cavity sealing member 10 expands faster and the front end part thereof in the direction of insertion tends to expand in the form of a conical with the apex 16 at the front end. Since, in the body cavity sealing member 10 for a rectum, the columnar part 17 thus expands faster than the apex 16, the body cavity sealing member 10 is immediately prevented from sliding out of the rectum G, which effectively prevents leakage of body fluids.

The above embodiment employs the body cavity sealing member 11 for a rectum having a size of 22 mm diameter and 80 mm length. The body cavity sealing member of the present invention, however, is not limited to this. As the body cavity sealing member has a smaller diameter, it is more easily inserted through the anus H into the body cavity (rectum G). In this case, a problem arises that it takes long time until the body cavity sealing member swells to expand up to a size that comes into tight contact with the rectum wall since it is inserted in the rectum. On the contrary, if the diameter of the body cavity sealing member is too large, it is hard to insert into the anus H. Therefore, the diameter of the body cavity sealing member is preferably 10 to 25 mm. Further, as the body cavity sealing member has a smaller length, it is more easily inserted into the rectum G. However, if the length of the body cavity sealing member is too small, it comes short of the volume for swelling, thereby degrading its sealing function. Therefore, the length of the body cavity sealing member is preferably 40 to 110 mm. More preferably, the length of the body cavity sealing member is 60 to 95 mm.

In the body cavity sealing member 11, since the core of the inner layer 12a of each of superabsorbent fibers 12, which are components of the body cavity sealing member 11, keeps the shape of a fiber after absorbing water, the columnar part 17 retains a substantially columnar shape or the shape conforming to the inner wall of the rectum G also after expanded and is securely held in the rectum G. Further, when absorbing water to rapidly expand in the radial direction, the body cavity sealing member 10 promptly comes into tight contact with the passage inner wall of the rectum G and exhibits sealing performance, which is advantageous. For this purpose, the superabsorbent fiber 12 used is preferably of a type that expands up to 2.5 or more times its diameter by absorbing water, more preferably of a type that expands up to 5 or more times its diameter, and still more preferably of a type that expands up to 10 or more times its diameter. Since larger diameter expansion means higher water absorption capacity, more largely expandable fibers are preferable. In particular, the superabsorbent fiber is preferably of a type that has an inner layer 12$a$ made of acrylonitrile-based polymer and having a degree of water swelling of 5 to 200 cc/g. If the outer layer 12$b$ contains carboxyl groups, this is preferable because they have adsorbability to ammonia and therefore can absorb odor. The content of carboxyl groups is preferably 0.5 to 4.0 mmol/g. The outer layer 12$b$ of the superabsorbent fiber 12 is obtained by treating an acrylic fiber with aqueous alkali metal hydroxide solution to hydrophilically crosslink only the outer layer of the acrylic fiber. Through such a treatment, carboxyl groups in alkali metal salt form are introduced into the acrylic fiber.

Figure 19:
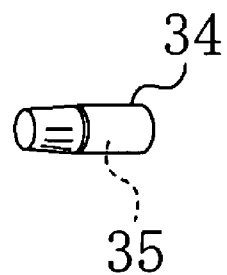
FIG. 19 shows a lubricant.
Figure 20:
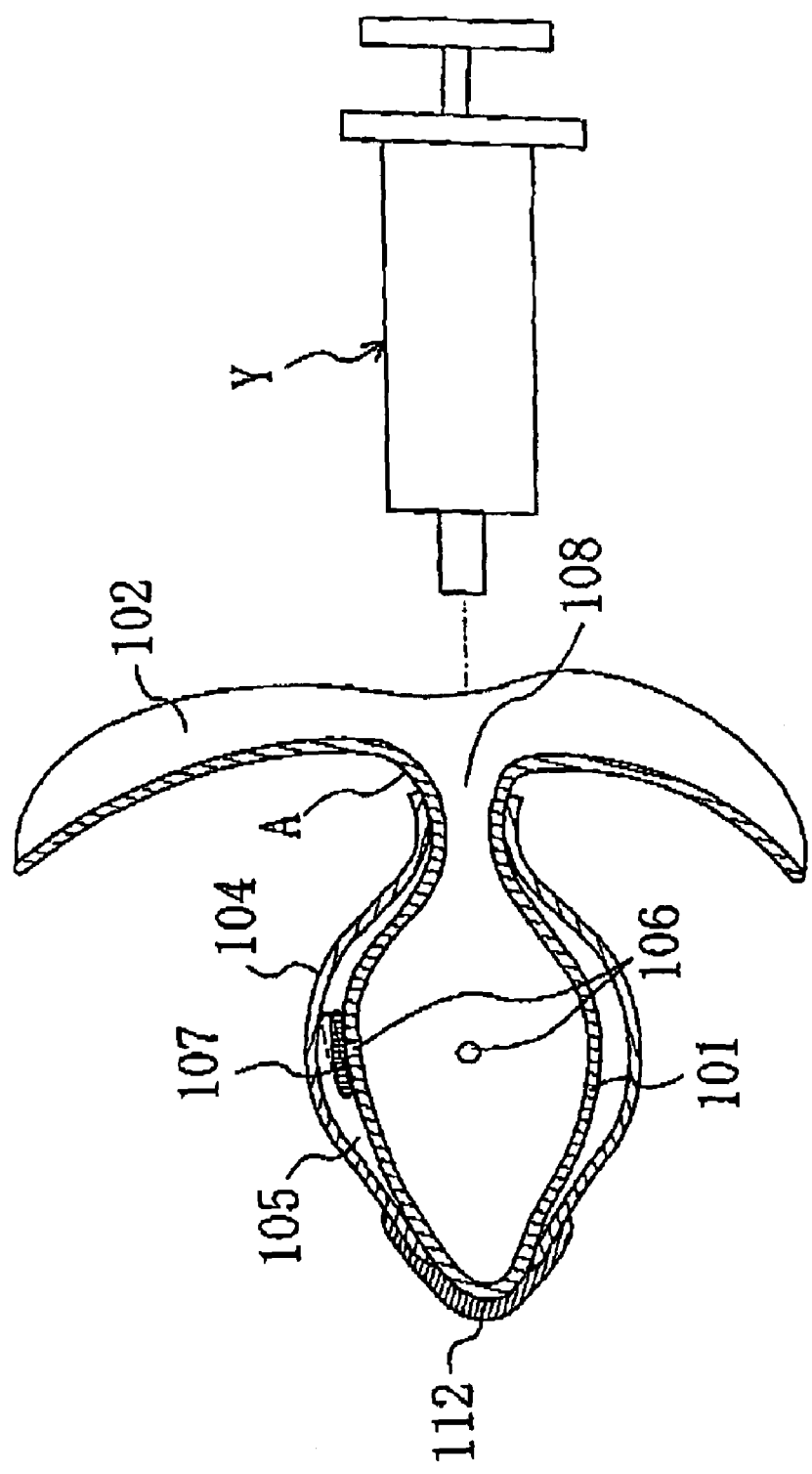
FIG. 20 shows a known art.
Figure 21:
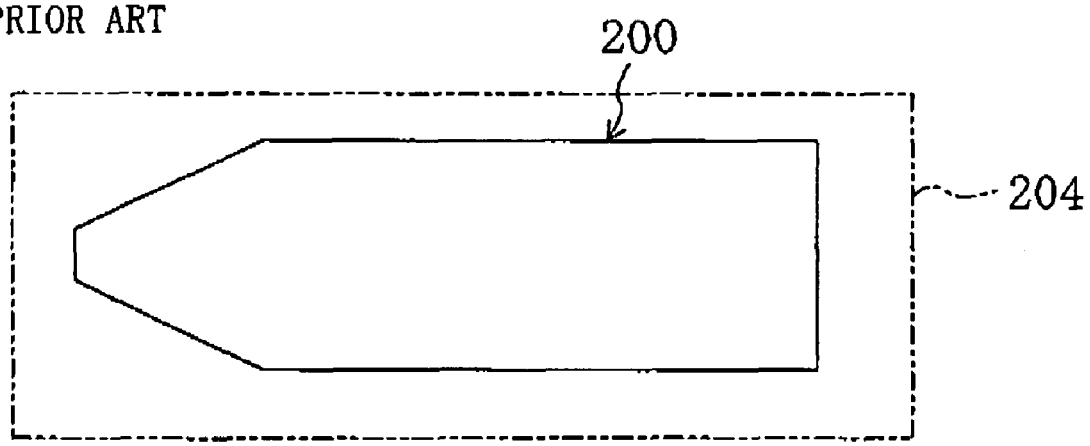
FIG. 21 shows another known art.
Figure 22:
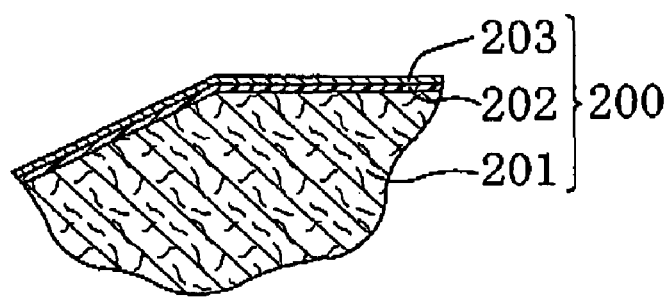
FIG. 22 shows a partly cross-sectional view of the known art shown in FIG. 21.

With the aim of preventing moisture absorption, preferably, the body cavity sealing member 10 is previously put in a sealed bag (for example, plastic or tinfoil bag) and the sealed bag is unsealed in use. The body cavity sealing member 10 is prepared in this state and, in use, the lubricant 35 in a separately prepared vessel 34 shown in FIG. 19 is applied to the outer surface of the molded object 11 (the cut surface 15 and the columnar part 17) in order to facilitate its entrance into the anus H. Glycerin in the vessel 34 is used as the lubricant 35. In order to avoid the possibility for glycerin to penetrate into the molded object 11 as much as possible, glycerin is preferably applied to the body cavity sealing member 10 immediately before use.

The reason why the end of the molded object 11 is tapered is that the body cavity sealing member 10 is made easy to insert into the anus H. Therefore, the tapered shape is not limited to that in the above embodiment. For example, the end of the molded object 11 may have a shape having an inclined surface at one side only or a shape having an inclined surface with different angles. Alternatively, the end of the molded object 11 is not conical but may have a plurality of inclined surfaces, such as polygonal surfaces. Alternatively, the end of the molded object 11 may be shaped in the form of elliptic cross section.

In the first embodiment, the tapered cut surface 15 is formed by a cutting blade. The cutting method is not limited to this but cutting may be carried out by other means such as scissors. Alternatively, cutting may be carried out using laser. When laser cutting is carried out, the heat treatment can be made concurrently.

In the above embodiment, the heat treatment is implemented by pressing the cut surface 15 against the recess of the heated die. The heat treatment is not limited to the method in the above embodiment but other heat treatment methods such as high-frequency induction heating may be used. Alternatively, after the end of the molded object 11 is roughly machined by a cutting blade, a previously heated cutting blade (or heating wire) for finish machining is used to subject the surface of the end to heat treatment concurrently with finishing cut. Alternatively, the heat treatment and cutting of the end of the molded object 11 may be implemented at once using, for example, a heating wire.

Other Embodiments

Figure 14:
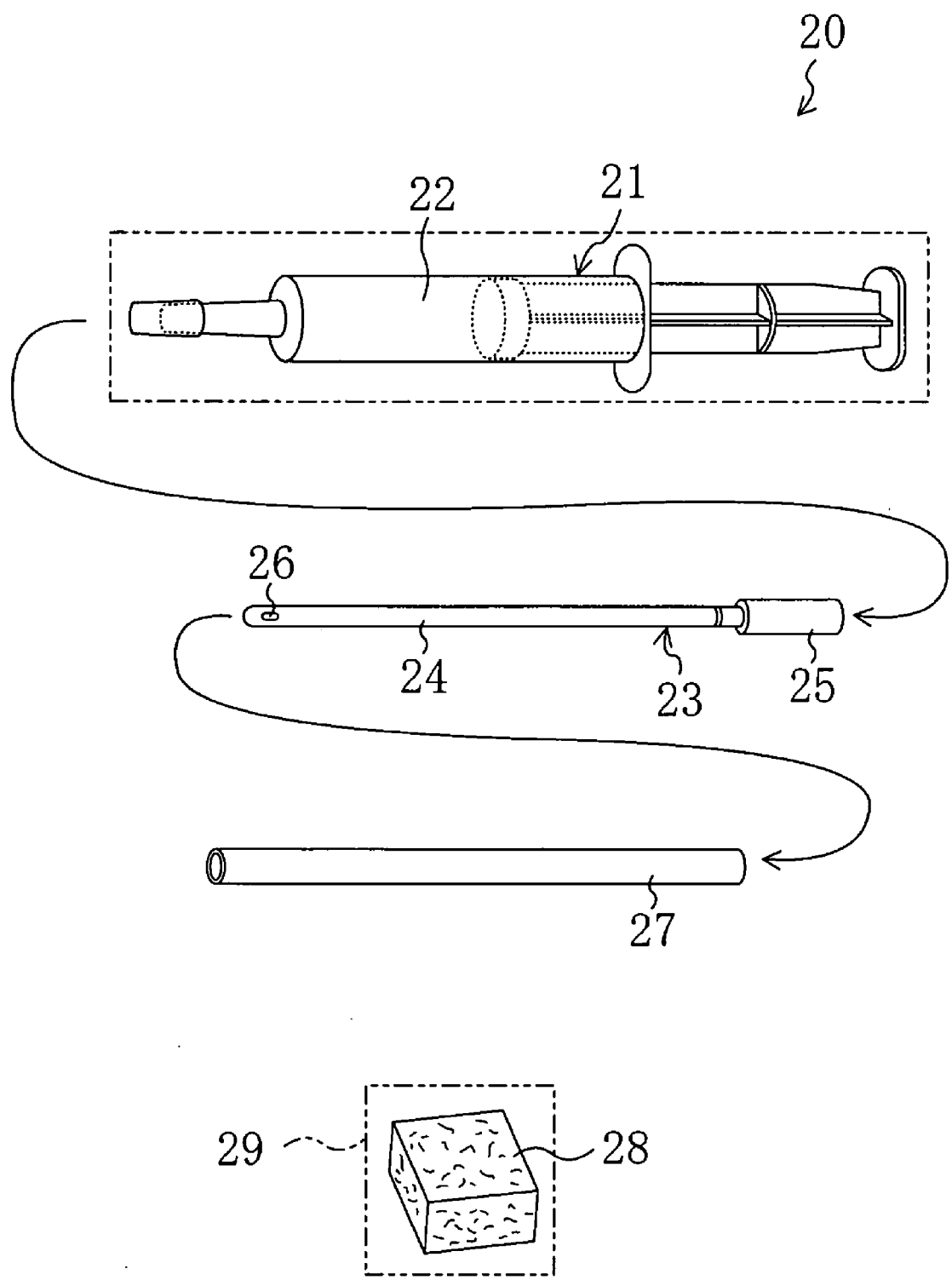
FIG. 14 shows an example of a corpse treatment device used with the body cavity sealing device for a corpse of the present invention.
Figure 15:
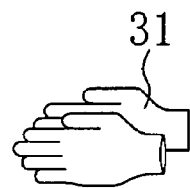
FIG. 15 shows equipment additionally used as a component of the corpse treatment device of the present invention.

FIG. 14 shows a corpse treatment device 20 in which, aside from the above body cavity sealing member 10, other equipment for sealing body cavities of a corpse, such as the throat and mouth, is collected.

In this example, the corpse treatment device 20 includes a syringe 21 for sealing a throat through a nostril, and an insertion tube 23 which is fittable to the distal end of the syringe 21 and then inserted into the nostril. The syringe 21 is filled with a jelly substance 22 in which superabsorbent resin powder is dispersedly mixed. The insertion tube 23 includes a tube body 24 and a connecting part 25 located at the rear end of the tube body 23 and connectable to an infusion head of the syringe 21, and has a tube opening 26 located at the distal end of the tube body 23. Reference numeral 27 denotes a cover member for covering the insertion tube 23.

The superabsorbent resin powder is preferably dispersed at 5,000 or more particles/ml in the jelly substance 22, and the jelly substance 22 preferably contains 0.02 to 0.15 parts by weight of a thickener per 100 parts by weight of solvent and has a viscosity of 8,000 to 40,000 CP. More preferably, superabsorbent fine particles are dispersed at 17,000 to 29,000 particles/ml in the jelly substance 22. Still more preferably, superabsorbent microparticles formed of 20 to 150 mesh particles are dispersed at 18,000 to 25,000 particles/ml in the jelly substance 22.

Preferably, the jelly substance 22 in the syringe 21 contains at least 1 of ethylene glycol, propylene glycol, diethylene glycol, methanol, ethanol and glycerin, also contains 0.01 to 1.0 parts by weight of an acrylic acid polymer and 0.03 to 0.7 parts by weight of a neutralizer per 100 parts by weight of an alcohol-based principal component, has a viscosity of 8,000 to 40,000 CP and has a PH of 6 to 8. The present invention can employ, as structures of the syringe 21 filled with the jelly substance 22 and the insertion tube 23 and the composition of the jelly substance 22, those disclosed in Japanese Unexamined Patent Publication No. 2002-275001. Therefore, a further description thereof will not be given here.

Reference numeral 28 denotes a cotton piece, which will be put in a mouth. By putting such a cotton piece 28 in the mouth, body fluids such as saliva can be definitely prevented from leaking out. In addition, when two such cotton pieces 28 are positioned in both cheeks, respectively, the cotton pieces swelled by absorbing body fluids exhibit a good function to fair the shapes of both cheeks. In particular, when dentures are taken out of the corpse of an old person, the cheeks collapse, leading to a poor looking face. However, when the cotton pieces 28 are positioned within the cheeks, they appropriately swell and hence the cheeks can be kept in appropriate shapes. The cotton piece 28 is not limited to a pure cotton piece. Preferably, 0.5 to 2.0 g of jelly substance is contained in a cotton piece of 4 cm by 4 cm. In this case, four to five plies of cotton pieces of 4 cm by 4 cm are preferably prepared. The cotton piece 28 is contained in a container 29 formed of a sealed bag. The body cavity sealing member 10, the syringe 21, the insertion tube 23, the cover member 27 and the cotton piece 28 is contained in an unshown bag. Thus, all necessary items are kept on hand to prevent leakage of body fluids from cavities of a corpse in treating the corpse, particularly, all items for treating cavities in a lower body, such as the anus or virginal cavity, the throat and the mouth are kept on hand.

Therefore, the treatment for preventing leakage of body fluids from a corpse can be successfully implemented in a short time.

FIGS. 15 to 18 show equipment that may be additionally contained in the bag for containing the corpse treatment device of the present invention.

FIG. 12 shows rubber gloves 31, which are used in handling equipment of the corpse treatment device, such as a body cavity sealing member 10 and a syringe 21, and handling the corpse. The addition of the rubber gloves 31 eliminates the need to look for necessary gloves for sanitation of a worker and surely prevents infection or the like to increase safety.

Figure 16:
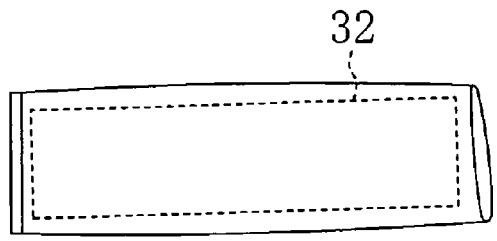
FIG. 16 shows another equipment additionally used as a component of the corpse treatment device of the present invention.

FIG. 16 shows a paper-made wet tissue 32 for wiping hands, which includes chlorine dioxide as a disinfectant. This is used by a worker during or after treating a corpse in order to simply wipe his/her hands. The wet tissue 32 for wiping hands is contained in a plastic sealed bag. The addition of the wet tissue 32 for wiping hands prevents infection to increase safety.

Figure 17:
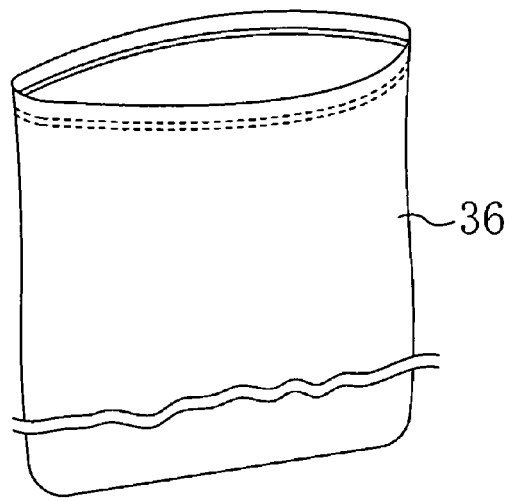
FIG. 17 shows still another equipment additionally used as a component of the corpse treatment device of the present invention.

FIG. 17 shows a container bag 36, which is for containing the bag containing the body cavity sealing member 10, the syringe 21, the insertion tube 23, the container 29, the cover member 27 and the like after treating a corpse. The container bag 36 is subjected to anti-leaching treatment to avoid leaching of body fluids and the like of the corpse. Since these components are contained in the container bag 36, they are prevented from being scattered and causing contamination and infection.

Figure 18:
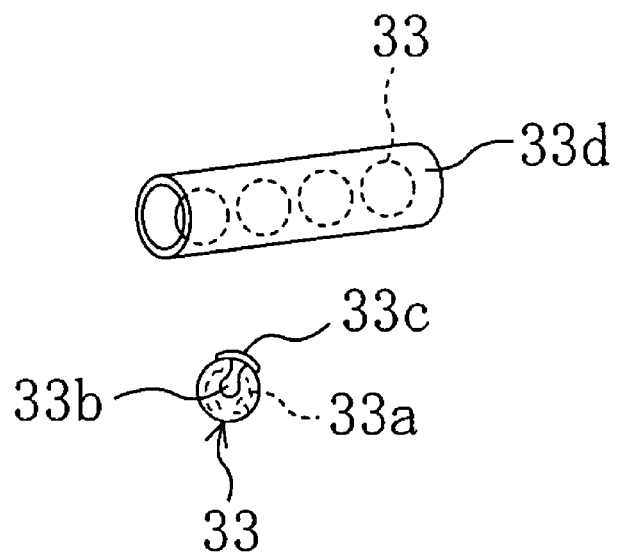
FIG. 18 shows earplugs and nose plugs additionally used as components of the corpse treatment device of the present invention.

FIG. 18 shows sealing members 33 for use as earplugs or nose plugs. Four sealing members 33 are provided in total, two as earplugs and two as nose plugs. Each sealing member 33 is made of a spherical cotton material 33a, which contains, in its center, a jelly substance 33b containing superabsorbent resin, namely, a jelly substance identical to the jelly substance 22 in the syringe 21. Reference numeral 33c denotes a cap member. The sealing members 33 are contained in a cylindrical, plastic, sealed bag 33d. The addition of the sealing members 33 further securely prevents body fluids from leaking out. Merely a small amount of body fluid leaks from an ear, and a very small amount of body fluid leaks from a nose when the aforementioned body fluid anti-leakage treatment for a throat is performed. Therefore, a sealing member simply made of a cotton material 33b may be used as a simple type of sealing member. Though in this embodiment the sealing member 33 is contained in the cylindrical, plastic, sealed bag 33d, it may be contained in the plastic sealed bag 29 together with the cotton piece 28 for a mouth.

FIG. 19 shows a lubricant 35 and a vessel 34 therefor. When the lubricant 35 is applied to the outer surface of the body cavity sealing member 10 and the insertion tube 23, they can be smoothly inserted into a body cavity of a corpse. If the lubricant 35 is prepared together with the corpse treatment device and its equipment in this manner, the oblivion of its application can be prevented thereby saving the trouble of looking for lubricant.

Further, necessary items for treating a corpse, such as gauze, absorbent cotton, a disinfectant, a deodorant and a diaper, may be prepared together in a kit. Thus, the work for corpse treatment can be smoothly carried out. Furthermore, another additional equipment may be added, such as a female urethra sealing member, a deodorant, face gauze for a corpse, a band for fixing the jaw of a corpse, a band for joining the hands of a corpse and the like.

A preferable superabsorbent resin-containing jelly substance to be inserted into a throat is one disclosed in Japanese Unexamined Patent Publication No. 2002-275001 and, therefore, its detailed description will not be given here. For example, glycerin or vaseline is used at the lubricant.

The sealing member for an earplug and a nose plug preferably contains, in the cotton material, 0 to 1.5 mg of jelly substance containing superabsorbent resin. The cotton piece for a mouth preferably contains 0.5 to 2.0 g of jelly substance per 4 cm by 4 cm piece. These jelly substances used are preferably the same as the jelly substance for a throat.

The body cavity sealing member may contain at least one of commonly known deodorants and disinfectants. Likewise, the jelly substance in the syringe for a throat may contain at least one of commonly known deodorants and disinfectants. Preferably, a disinfectant is permeated into the paper sheet for wiping hands.

The body cavity sealing member of the present invention is a columnar molded object formed of porous fiber elements of double-layer structure having an inner layer which is a core made of an acrylic fiber and a superabsorbent outer layer formed to surround the inner layer. The porous fiber elements rapidly absorb water to swell on contact with body fluids in a body cavity and thereby expands up to approximately 2.5 or more times its diameter. The body cavity sealing member is formed by cutting an end part of the columnar molded object to taper toward the end thereof and the cut edges of porous fiber elements exposed at the cut surface of the end part are processed to form a smooth surface. Therefore, the sealing member can be smoothly inserted into a body cavity of a corpse to fully get in. Once inserted, the sealing member immediately absorbs body fluids and expands to come into tight contact with the inner wall of the body cavity. Therefore, the expanded sealing member can be held in the body cavity and can surely prevent body fluids from leaking out of the body cavity. In particular, since the cut edges of cut fiber elements in the tapered part are processed to provide a smooth surface, this prevents the fiber elements from resisting insertion of the sealing member. Therefore, anyone can easily carry out the insertion work.

With a simple process of heat treatment, the cut edges of porous fiber elements exposed at the cut surface melt at the uppermost surfaces to change into smooth surfaces. Therefore, the sealing member can be easily inserted into a body cavity.

In addition, since it takes much time for the lubricant such as glycerin applied to the tapered part before insertion to penetrate inward from the surface, this contributes to the ease of the insertion work.

Further, since the tapered part is hardened by heat treatment, it becomes less likely to deform. Therefore, there is almost no possibility that the end part deforms or folds during insertion, which facilitates the insertion work.

If the tapered part is fused by heat treatment, it is less likely to absorb body fluids when the body cavity sealing member is inserted in a body cavity and absorbs the body fluids to expand. Thus, the columnar part not subjected to heat treatment absorbs body fluids to expand earlier so that the fiber elements expand in the form of a sector. Therefore, the body cavity sealing member is surely prevented from sliding out of the body cavity and the body cavity can be rapidly sealed.

In the corpse treatment device of the present invention, all necessary items are kept on hand in order to prevent leakage of body fluids from cavities of a corpse in treating the corpse, particularly, all items for treating cavities in a lower body, such as the anus or virginal cavity, the throat and the mouth are kept on hand. Therefore, the treatment for preventing leakage of body fluids from a corpse can be successfully implemented in a short time.

According to the method for manufacturing a body cavity sealing member of the present invention, an end part of the columnar molded object is cut to taper toward the end thereof and then heat-treated in a predetermined temperature range for s predetermined time to have a smooth surface. Therefore, the insertion work can be facilitated, which enables even less experienced persons to easily insert the body cavity sealing member into a body cavity of a lower body. In particular, since there is no need to cover the sealing member with a water-soluble sheet or the like, this significantly reduces the number of manufacturing process steps and significantly reduces the manufacturing cost.

If the heat treatment is implemented by pressing the tapered end part of the body cavity sealing member against a die which has a recess for receiving the tapered end part of the body cavity sealing member and in which the surface of the recess is heated, the smoothness of the surface layer and the hardened surface layer can be attained by melting of fiber elements with a simple heat treatment. Therefore, the manufacturing method for the body cavity sealing member is easy, can be attained at low cost and allows mechanization and automation.

INDUSTRIAL APPLICABILITY

As described so far, the corpse's body cavity sealing member of the present invention can be used by even less experienced persons to easily carry out the work for preventing leakage of body fluids from a corpse and, therefore, is useful for corpse treatment.

The invention claimed is:

1. A body cavity sealing member to be inserted into a body cavity of a corpse to absorb body fluids, expand, reside in the body cavity, and seal a passage of the body cavity to prevent leakage of the body fluids, comprising
 a molded object formed of a plurality of fiber elements of double-layer structure molded into a substantially columnar shape, and the sealing member is formed such that at least one end part of the molded object is tapered toward the end thereof,
 a surface of the tapered end part being formed of distal ends of the fiber elements fused to another,
 each of the fiber elements including an inner layer which is a core made of an acrylic fiber and an outer layer which is formed to surround the inner layer and has a higher water-absorbability and higher swellability than the inner layer, and has the property of absorbing body fluids in the body cavity to expand up to approximately 2.5 or more times the diameter thereof, and
 wherein the surface of the tapered end part with fused distal ends of the fiber elements has a higher hardness than the surface of the remaining columnar part.

2. The body cavity sealing member of claim 1, wherein the surface of the tapered end part with fused distal ends of the fiber elements has a smaller coefficient of friction than the surface of the remaining columnar part.

3. The body cavity sealing member of claim 1, wherein the fiber elements exposed at the surface of the tapered end part are formed by heat treatment.

4. The body cavity sealing member of claim 3, wherein the heat treatment is implemented by melting the fiber elements exposed at the surface of the tapered end part to fuse one fiber element to another.

5. The body cavity sealing member of claims 1, wherein the outer layer of each of the fiber elements is made of hydrophilic cross-linked polymer, the inner layer thereof is made of acrylonitrile-based polymer, and each of the fiber elements has the property of absorbing body fluids to expand up to five or more times the diameter thereof and has a degree of water swelling of 5 to 200 cc/g.

* * * * *